United States Patent [19]

Stevens

[11] Patent Number: 4,798,586

[45] Date of Patent: Jan. 17, 1989

[54] METHOD AND APPARATUS FOR AIDING DILATATION CATHETERIZATION

[75] Inventor: Robert C. Stevens, Williston, Fla.

[73] Assignee: Cordis Corporation, Miami, Fla.

[21] Appl. No.: 36,223

[22] Filed: Apr. 9, 1987

[51] Int. Cl.[4] ............................................. A61M 29/00
[52] U.S. Cl. ........................................ 604/96; 604/52; 604/104; 604/22; 128/344
[58] Field of Search .............. 128/305, 344, 267, 772, 128/348; 604/51-53, 96-99, 22, 93

[56] References Cited

U.S. PATENT DOCUMENTS

| | | | |
|---|---|---|---|
| 2,548,602 | 4/1951 | Greenburg | 604/96 |
| 4,003,369 | 1/1977 | Heilman et al. | 128/772 |
| 4,020,847 | 5/1977 | Clark, III | 128/305 |
| 4,273,128 | 6/1981 | Lary | 128/344 |
| 4,323,071 | 4/1982 | Simpson et al. | 604/28 |
| 4,445,509 | 5/1984 | Auth | 128/305 |
| 4,545,390 | 10/1985 | Leary | 604/96 |
| 4,638,805 | 1/1987 | Powell | 128/344 |
| 4,646,719 | 3/1987 | Neuman et al. | 128/344 |
| 4,654,024 | 3/1987 | Crittenden et al. | 128/303.1 |
| 4,664,114 | 5/1987 | Ghodsian | 128/344 |
| 4,732,154 | 3/1988 | Shiber | 128/305 |
| 4,747,406 | 5/1988 | Nash | 128/305 |
| 4,747,821 | 5/1988 | Kensey et al. | 128/305 |
| 4,749,376 | 6/1988 | Kensey et al. | 128/305 |

FOREIGN PATENT DOCUMENTS 0189329 4/1986 European Pat. Off. .

OTHER PUBLICATIONS

USCI, Safety Spring Guides, Stainless Steel & Teflon Coated, Section 2, USCI, A Division of C. R. Bard Inc., Billerica, Mass. 01821.

Primary Examiner—C. Fred Rosenbaum
Assistant Examiner—Colleen M. Reilly
Attorney, Agent, or Firm—Watts, Hoffmann, Fisher & Heinke

[57] ABSTRACT

An improved technique for positioning a balloon dilatation catheter. When the balloon catheter approaches an obstruction that is difficult to enter, a drive catheter having a rotatable head is inserted into a central passageway in the catheter. The drive catheter bores through the obstruction allowing the balloon to be inserted and pressurized to compress obstructions and widen a passageway for blood flow.

9 Claims, 5 Drawing Sheets

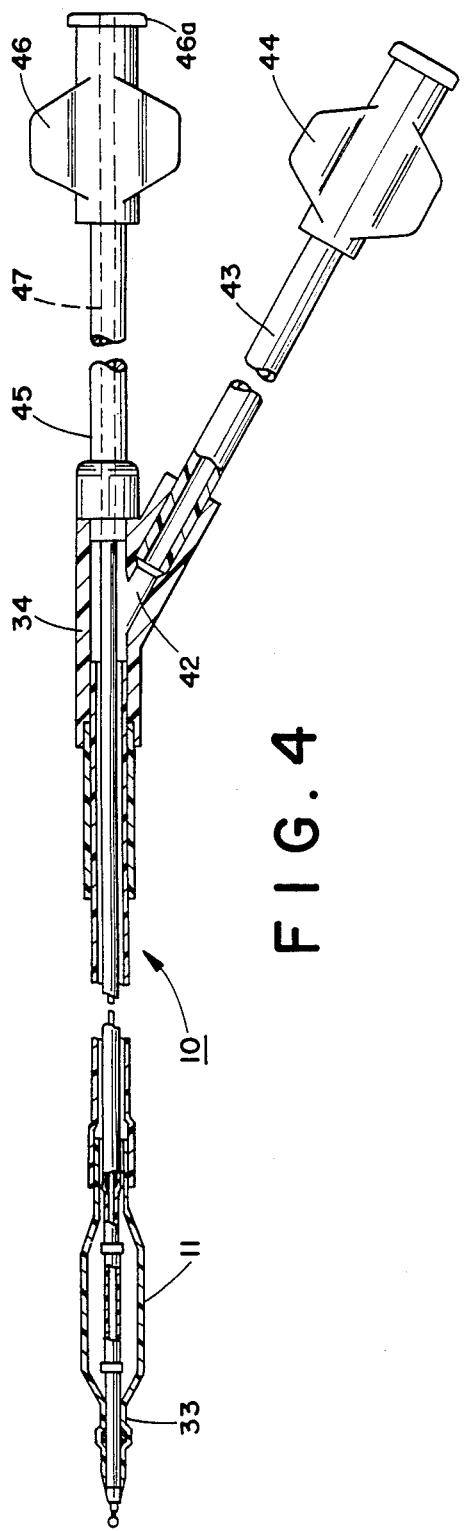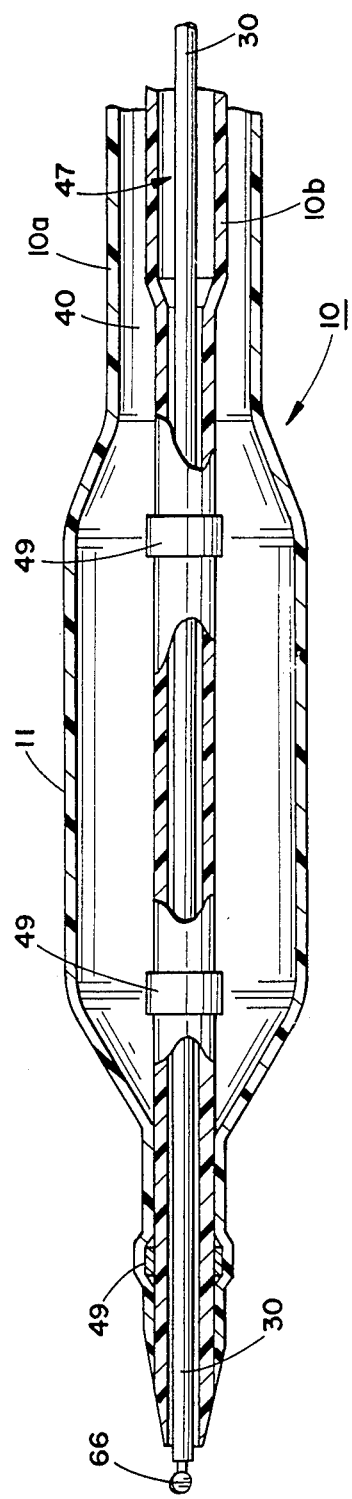

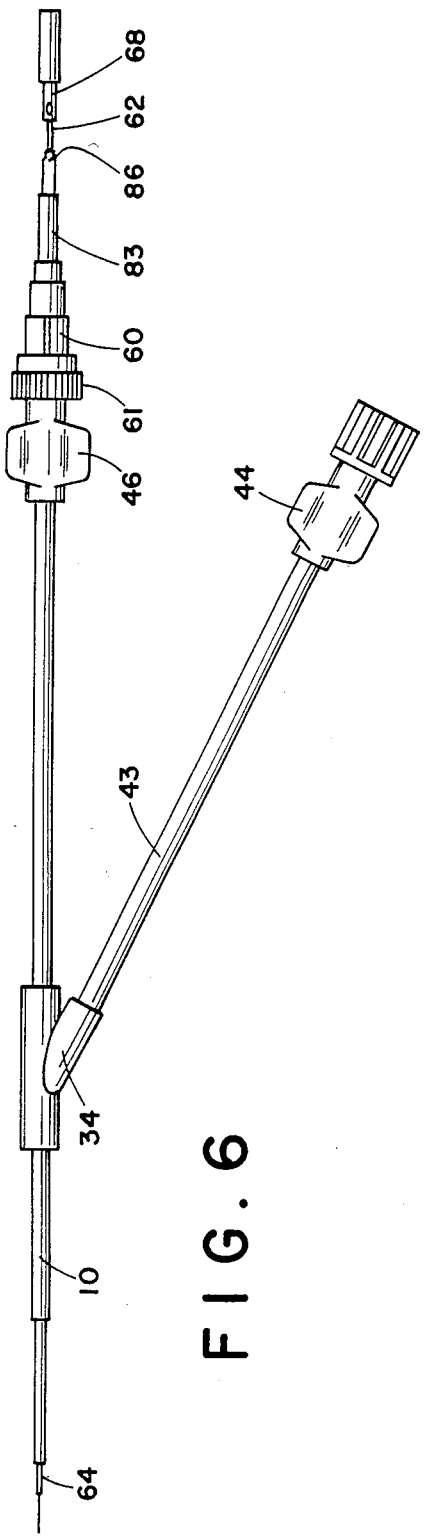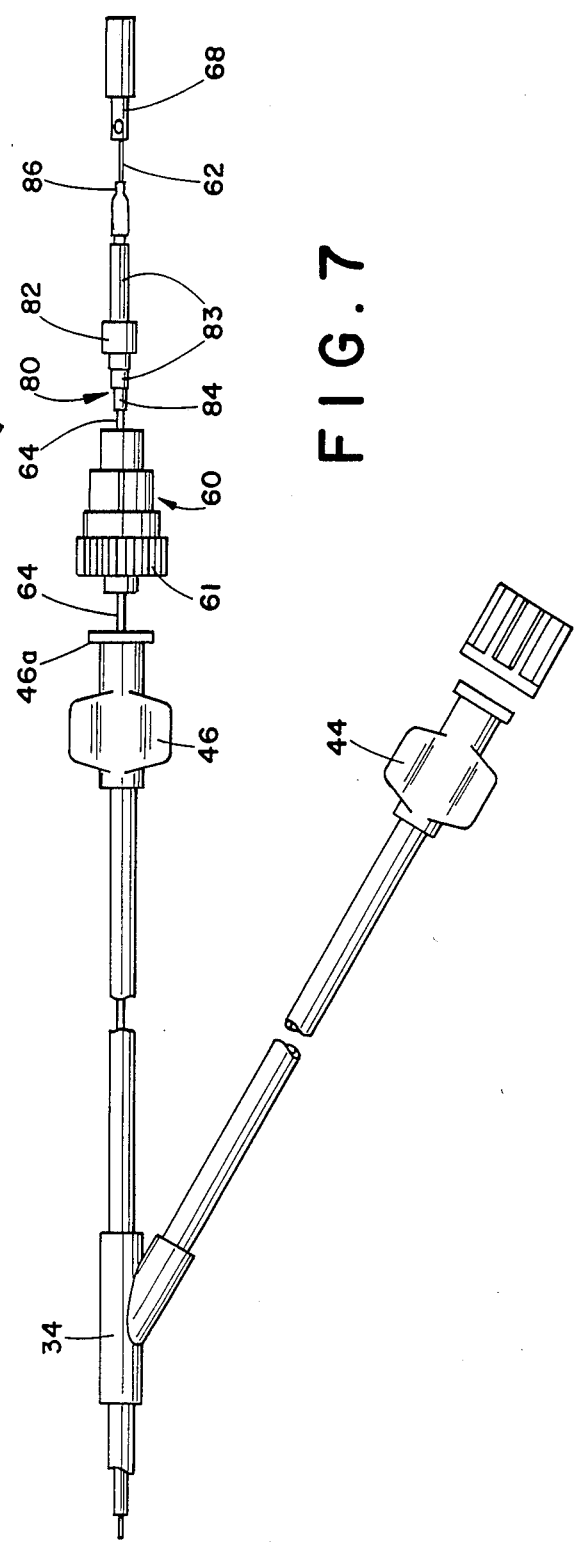

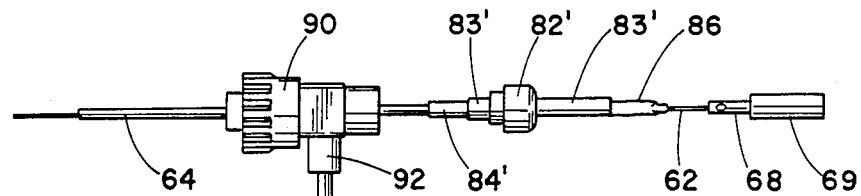
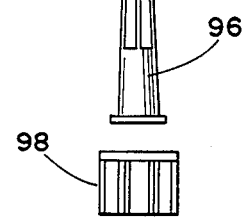
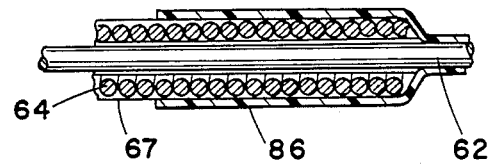
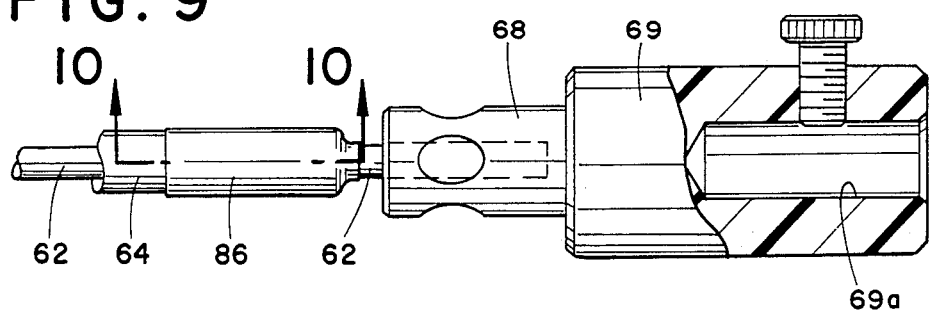
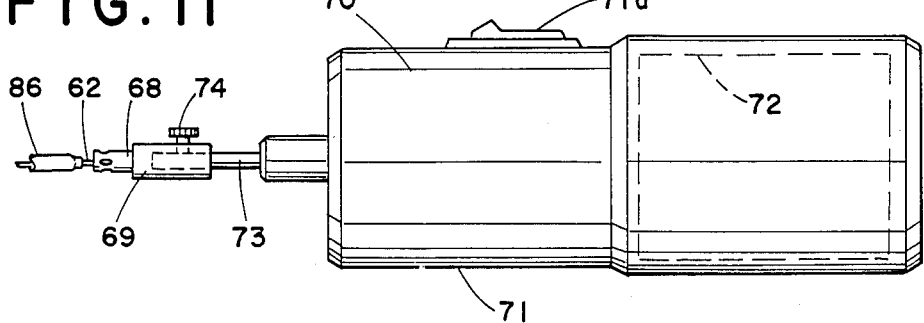

METHOD AND APPARATUS FOR AIDING DILATATION CATHETERIZATION

TECHNICAL FIELD

The present invention relates to method and apparatus for positioning a balloon dilatation catheter for use in opening blocked blood vessels.

CROSS REFERENCE TO RELATED APPLICATION

Commonly assigned patent application Ser. No. 027,186 filed Mar. 17, 1987 entitled "Catheter System Having a Small Diameter, Rotatable Drive Member" to Stevens discloses a drive catheter for use in opening a blocked blood vessel. The disclosure of this patent application is incorporated herein by reference.

BACKGROUND ART

Different non-surgical treatments of obstructive vascular disease are known. One of the first successful procedures receiving widespread acceptance was the use of a flexible catheter having a distensible balloon at its distal end. This so-called dilatation catheter is guided through an obstruction in the blood vessel and pressure is applied to the balloon, causing it to expand and compress lesions in the obstructed vessel.

The initial encouraging results produced with balloon catheters led Gruentzig to extend this technique to use in coronary arteries. A review of the use of balloon catheters for treatment of obstructive vascular disease in coronary arteries is presented in chapter 15 of *Cardiovascular Procedures Diagnostic Techniques and Therapeutic Procedures*, by Tilkian and Daily, C. V. Mosby Company, 1986, pp. 328–376. The chapter 15 disclosure of this text is incorporated herein by reference.

The method steps in conducting an angioplasty procedure are discussed in detail in the aforementioned text. Briefly, a guiding catheter is inserted and positioned so that the dilatation catheter can be guided into the region of blocked or reduced blood flow. A guidewire is inserted beyond the balloon catheter and manipulated by the physician until the guidewire enters the blocked blood vessel. The process of introducing the guidewire into an appropriate vessel can be very difficult, especially if the obstruction is complete or nearly so. The guidewire has such a small diameter and is so flexible it often buckles on impact with the obstruction.

Even if the physician successfully advances the guidewire through the obstruction, when the physician attempts to push the balloon through the obstruction, the diameter of the balloon may be such that the insertion is difficult or impossible. This is especially true, when deposits within the blood vessel that are blocking blood flow are rigid and do not yield to forces exerted by the balloon tip.

DISCLOSURE OF THE INVENTION

It is one object of the invention to improve the ability of a physician to open blocked blood vessels using a balloon catheterization procedure. The invention allows the balloon catheter to be more easily positioned within an obstructed region prior to inflation. As a result, vessels that were blocked to an extent heretofore untreatable with balloon catheterization can now be treated without surgical intervention.

A method of the invention includes the steps of positioning a balloon catheter in the vicinity of a totally or partially blocked blood vessel. This can, for example, be a portion of the coronary artery or other vessel. The positioning step is typically accomplished with a guiding catheter and guidewire. If the physician experiences no difficulty in pushing the guidewire and balloon catheter through the obstructed region, this is done and the balloon is inflated in accordance with accepted procedures.

If, however, the catheter can not be readily inserted through the obstructions, the guidewire is withdrawn from the catheter and a small diameter drive catheter is inserted through a passageway previously occupied by the guidewire. The drive catheter is energized and as its tip rotates at high speeds, the physician pushes it through the obstructions to create a passageway or lumen. As the drive catheter is pushed through the obstructions, the balloon catheter acts as a guide. The energized drive catheter is pushed through the obstructions a short distance, and then the balloon catheter inserted a short distance so that the drive catheter never extends too far ahead of the balloon. Once the drive catheter has opened a passageway through the deposits, the balloon is positioned within the deposits and inflated to compress those deposits and open a larger passageway for blood flow.

A drive catheter constructed in accordance with the invention includes a drive shaft supported within a flexible sheath and having a distal rotatable head for opening the initial passageway through the blocked region of the blood vessel. This rotatable head can be formed from a flattened end portion of the drive wire or alternately comprises an enlarged flattened tip attached to the drive wire. At the proximal end the drive catheter has a coupling for attaching the drive shaft to a motor for rotating the drive catheter tip at high speed.

From the above it is appreciated that one object of the invention is a new and improved catheterization technique allowing accurate and safe insertion of a dilation catheter through blocked regions of a blood vessel. This and other objects, advantages and features of the invention will become better understood from a detailed description of the invention which is described in conjunction with the accompanying drawings.

BRIEF DESCRIPTION OF THE DRAWINGS

FIG. 4 is a partially sectioned, elevation view of a balloon catheter;

FIG. 5 is an enlarged, partially sectioned view of the distal end of a balloon catheter having a drive catheter inserted for guiding the balloon through blood vessel obstructions;

FIG. 6 is an elevation view of the proximal end of a balloon catheter with a drive catheter inserted;

FIG. 7 is an exploded view of the FIG. 6 balloon catheter proximal end showing the components of a drive catheter and an adapter for connecting the drive catheter to the balloon catheter;

FIG. 8 shows an alternate drive catheter adapter for use with a balloon catheter that includes a side branch for dye injection, flushing, and blood pressure monitoring;

FIG. 9 is an enlarged partially sectioned view of the proximal end of the drive catheter;

FIG. 10 is a view as seen from the plane defined by the line 10—10 in FIG. 9 and illustrates a seal located at the proximal end of the drive catheter;

FIG. 11 schematically depicts a drive motor for energizing the drive catheter.

BEST MODE FOR CARRYING OUT THE INVENTION

Figure 1:
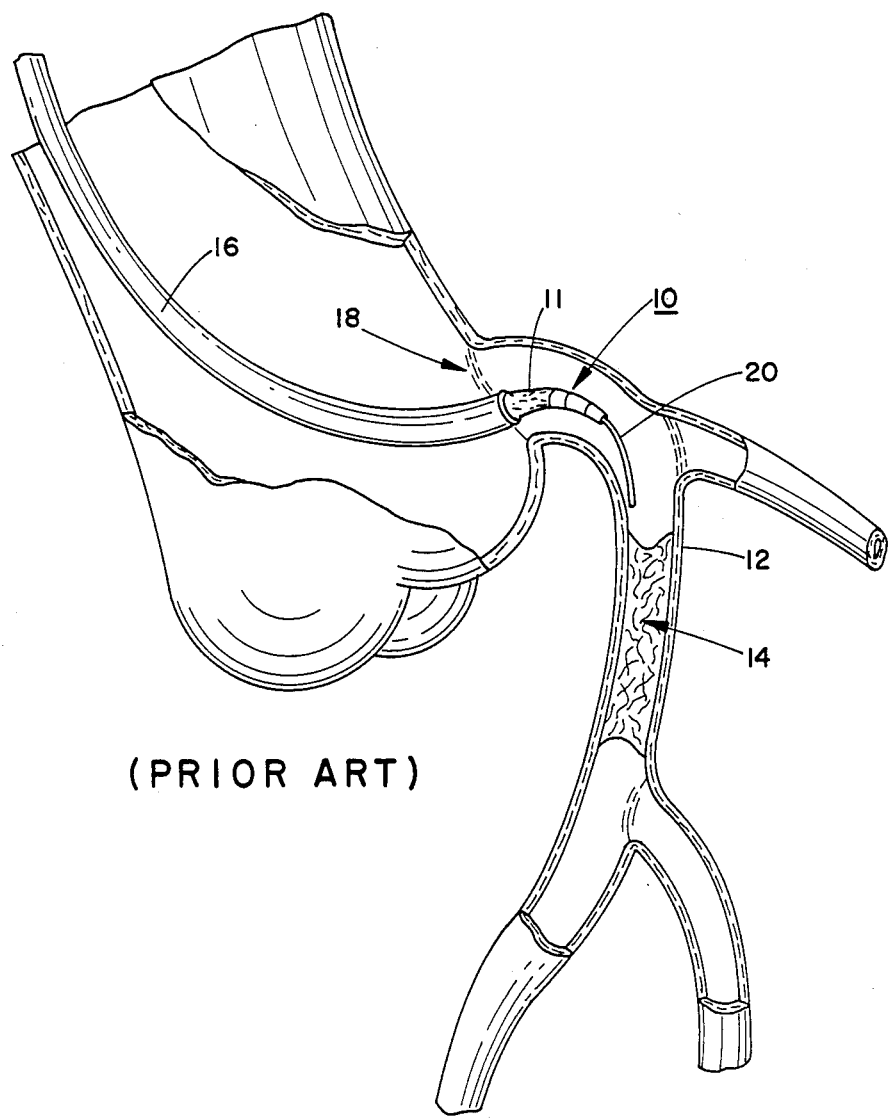
FIG. 1 is a schematic representation of a guiding catheter routing a dilation or balloon catheter into a blocked region of the left coronary artery.

Turning now to the drawings, FIG. 1 schematically shows a dilatation or balloon catheter 10 including an inflatable balloon 11 as an attempt is made to insert the balloon catheter 10 into a branching coronary artery 12 exhibiting a reduced blood flow due to a severe blockage obstructions 14. To insert the balloon catheter into this branching vessel 12, a physician inserts a guide catheter 16 to an entrance 18 of the coronary artery and then inserts the balloon catheter through the guiding catheter 16. Once the guiding catheter has been positioned, a guidewire 20 extending through the balloon catheter is used to guide the catheter 10 to the branching vessel 12.

The FIG. 1 illustration of the balloon catheterization insertion technique shows a prior art method. The deflated balloon is pushed through the obstructions 14 with the aid of the guidewire 20. When the obstructions 14 are rigid, it is difficult or impossible to properly position the catheter 10 for inflation.

Figure 2:
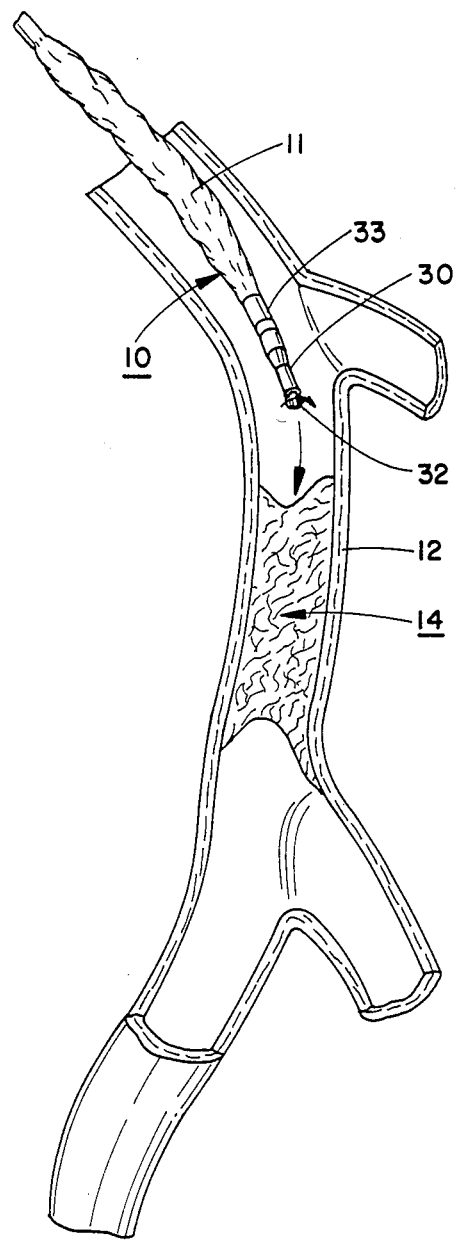
FIG. 2 shows a drive catheter approaching a blocked region of a blood vessel.
Figure 3:
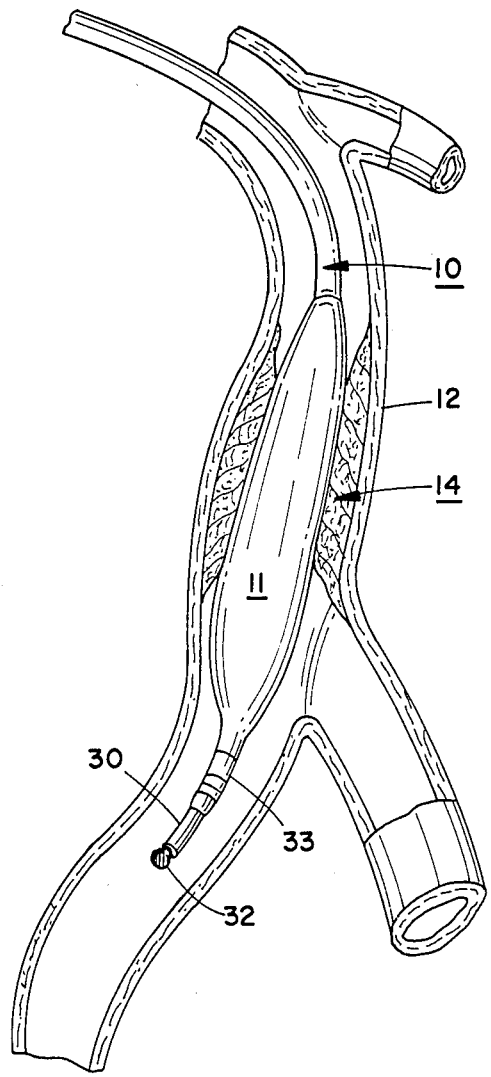
FIG. 3 shows a balloon catheter that has been pushed through obstructions within the blood vessel and inflated to compress those obstructions.

FIGS. 2 and 3 illustrate the present invention and its use of a drive catheter 30 for forming a pathway through the obstructions 14 to allow insertion of the balloon catheter 10. The drive catheter 30 is pushed through a central passageway in the balloon catheter 10 (occupied by the guidewire 20 in the prior art technique) and guided into the branching vessel 12. At its distal end the drive catheter 30 defines a rotatable head 32 that is used to bore an opening through the obstruction 14. A tapered distal end or tip 33 of the balloon catheter 10 is used as a guide to prevent this rotating head from moving from side to side as the head bores through the obstructions 14. The drive catheter 30 is opaque to x-radiation and the catheter 10 includes tip markers 49 so that as the drive catheter 30 is routed through the obstructions 14, a physician can monitor progress of the head as well as the balloon catheter.

Turning now to FIG. 4, a conventional balloon catheter 10 having a bifurcated "Y" proximal fitting 34 defines two passageways leading from the proximal fitting 34 to the distal balloon catheter tip 33. An outer sheath 10a and an intermediate sheath 10b of the catheter 10 defines an air passageway 40 (FIG. 5) leading from an air inlet 42 to the balloon 11. A side arm 43 coupled to the bifurcated proximal fitting 34 of the catheter 10 includes a leur hub fitting 44. When the balloon is properly positioned compressed air is injected into this passageway 40 to inflate the balloon 11.

A second in-line branch 45 coupled to the proximal fitting 34 includes a second leur hub fitting 46 and defines a central passageway 47 passing completely through the balloon catheter to the catheter's distal tip 33. This passageway 47 accommodates a guidewire during insertion of the balloon and in addition, can be used to inject dye through a center passageway 47 into the blood vessel via the catheter tip 33. Radio-opaque markers 49 are seen (FIG. 5) positioned along the distal end of the catheter 10 to aid a physician in monitoring the balloon catheterization procedure.

Additional details regarding the construction of balloon catheters and alternate designs for these catheters are found in the aforementioned and incorporated text to Tilkian et al.

In the event the physician conducting the balloon catheterization procedure experiences difficulty in properly positioning the catheter 10, the drive catheter 30 is substituted for the guidewire 20. Since in certain circumstances, the physician would already be aware that difficulty in placing the catheter is to be anticipated, the balloon catheterization procedure can also begin with the drive catheter 30 in place.

An elongated drive catheter 30 extends through a leur fitting adapter 60 (FIG. 6). The adapter 60 defining a through passage to accommodate the drive catheter 30 and includes a connector 61 that defines an internal thread to engage a flanged end 46a of the leur fitting 46. The drive catheter 30 includes a drive wire 62 rotatable mounted within a sleeve bearing 64 that passes through the adapter 60. The flattened rotating head 32 is formed at the distal end of the drive wire 62 and a drive bushing 68 is crimped onto the proximal end of the drive wire 62.

The drive catheter 30 can be constructed to include a range of diameters and utilize rotating heads 32 of different shape and size. In one embodiment of the invention, the rotating head 32 comprises a piece of stainless steel hypodermic tubing that is flattened and welded at the distal end of the drive wire 62. In other application, the end of the drive wire is flattened to form the rotating head. Since the catheter 30 must fit within existing passageways in conventional balloon catheters, an O.D. of 0.016 inch or less is used.

The sleeve 64 comprises a tightly coiled wire wound on a mandrel and coated with a thin (0.001 inch) teflon coating 67 (FIG. 10) to make the sleeve 64 lubricious so it slides through the balloon catheter passageway 47. Once the wire has been wound about the mandrel and teflon coated, it is separated from the mandrel and defines a flexible tube or sheath having a central passageway for receipt of the drive wire 62. When so formed, the drive wire is inserted through the sleeve 64 and the rotating head 32 and drive bushing 68 attached (or formed) at opposite ends of the drive wire 62. Additional details regarding the drive catheter construction are disclosed in the aforementioned and incorporated patent application to Stevens.

The drive bushing 68 is also crimped to a motor coupling 69 having a cylindrical opening 69A to accommodate an output shaft of a small drive motor 70. The motor 70 is mounted in an easily manipulatable handheld unit 71 (FIG. 11) having a switch actuator 71A and a conventional low voltage d.c. battery 72. A motor output shaft 73 is inserted into the coupling 69 and tightened by locking a locking screw 74 to transmit rotational motion to the drive wire 62. Rotational speeds of up to 30,000 rpm. are deemed to be desirable in guiding the balloon catheter through obstructions and commercially suitable motors having either variable speed adjustments for constant speed outputs are known.

Turning now to FIG. 7, the exploded view of the adapter 60 shows an interior seal 80 within the adapter for preventing the escape of fluid within the center passageway 46. A plastic bushing 82 fits over and is fixed to a plastic tube 83 through which the drive catheter 30 extends. During fabrication of the adapter 60, the drive catheter 30 is pushed through the tube 83 and a teflon sleeve 84 is slipped over the drive catheter 30 and then heat treated to cause it to shrink about the catheter 30. The teflon sleeve 84 is then pressed into the tube 83 and forms a fluid seal between the tube 83 and the teflon coated sleeve 64 of the drive catheter 30. The plastic bushing 82 is then solvent bonded to the adapter 60 to secure the teflon sleeve 84 within the adapter. The drive catheter 30 is then free to slide back and forth through the adapter 60 but fluid in the center passageway 46 does not leak through the adapter 60 along the outer surface of the drive catheter sleeve 64.

A second seal 86 (FIG. 10) at the proximal end of the drive catheter 30 prevents fluid that may enter the drive catheter from leaking from the drive catheter. This seal 86 comprises a teflon sleeve heat shrunk around the drive wire 62 and the proximal end of the sleeve 64. The seal 86 extends approximately one or two inches along the sleeve 64. High speed rotation of the drive wire 62 is minimally impeded by frictional contact between the seal 86 and drive wire 62.

Both the hand-held unit 71 and drive catheter 30 are stored in sterilized packages and are intended to be disposable so that for each new procedure new sterilized equipment is used. This reduces the chance of contamination from one procedure to the next.

FIG. 8 illustrates an alternate adapter 90 for routing the drive catheter 30 into the balloon catheter 10. This adapter 90 includes a seal 84', plastic bushing 82', and tube 83' to prevent fluid from leaking past the drive catheter. In addition, the adapter 90 includes a side branch 92 which leads via a tube 94 to a fitting 96. The fitting 96 includes an end cap 98 which can be removed to allow radio-opaque dye to be injected into and through the center passageway 47 in the balloon catheter 10 as the drive catheter is rotated at high speed to open a passageway. In addition, suction can be applied via this side branch 92 to remove debris and deposits which may break loose during the insertion of the drive catheter. Finally, the side branch 92 can also be used to monitor blood pressure in the obstructed vessel.

Operation

A physician conducting a balloon catheterization procedure encounters difficulty placing the balloon 11 through a blood vessel obstruction and this placement will be facilitated by practice of the present invention. The drive catheter 30 is withdrawn from a sterilized package and inserted into the proximal end of the catheter 10. Since the drive catheter sheath 64 slides back and forth through the adapter 60, the adapter is attached to the leur fitting 46 and the physician pushes the drive catheter 30 through the passageway 47 and out the distal tip 33 of the balloon catheter 10. Throughout the procedure, the balloon catheter 10 is used as a guide for the drive catheter 30. The rotatable head 32 is brought in proximity to the obstruction and energized by activating the motor. As the rotating head 32 rotates at high speeds, the physician brings it into contact with the obstruction 14 to open a passageway for balloon catheter insertion. Both the balloon catheter tip 33 and rotating head 32 are pushed ahead in a coordinated fashion. First the rotating head is pushed into the obstruction and then the catheter 10 pushed forward. This coordinated movement of the two catheters allows the balloon catheter 10 to guide the driven catheter 30 in movement through the obstruction. Once an entryway has been formed by practice of the invention, the balloon catheter is placed in a bridging configuration and pressure applied to the balloon to inflate and compress lesions within the blood vessel.

Throughout the procedure, suction may be applied to remove pieces of the obstruction as they are dislodged and both pressure monitoring and dye injection can occur through the side arm adapter 90. It is also anticipated that different size drive catheters 30 will be available for use in different applications. It is also contemplated that different diameter drive catheters 30 be used in the same procedure as needed. Once the balloon has been inflated to widen a passageway for blood flow, it is deflated and both the drive catheter 30 and dilatation catheter 10 are withdrawn. Since the drive catheter need not be in place during balloon inflation it may be withdrawn prior to this step to create a wider passageway for dye injection, pressure monitoring, or suction.

The present invention has been described with a degree of particularity. It is the intent, however, that the invention include all modifications and alterations from the disclosed design falling within the spirit or scope of the appended claims.

I claim:

1. A procedure for opening a blocked or partially blocked vessel comprising the steps of:
   positioning a balloon catheter having a central passageway extending therethrough into proximity to a region of deposits that cause reduced blood flow in the blood vessel;
   inserting an elongated rotatable member through the central passageway of the balloon catheter to cause a distal end of the rotatable member to extend beyond the balloon catheter and approach said deposits;
   rotating the rotatable member relative the balloon catheter while bringing the distal end of the rotatable member into contact with the deposits to open a lumen through said deposits;
   pushing the balloon catheter through the lumen opened by the distal end of the rotatable member to position the balloon within the deposits;
   inflating the balloon to widen the lumen; and
   deflating the balloon and withdrawing said balloon catheter from the blood vessel.

2. A process for opening a partially or totally blocked blood vessel comprising the steps of:
   inserting an elongated dilatation catheter having an inflatable balloon at a distal end into the patient blood vessel;
   routing the dilatation catheter through the blood vessel to bring the balloon into proximity to deposits that reduce blood flow within the blood vessel;
   inserting an elongated rotatable drive having a rotatable head at one end through the elongated dilatation catheter to position said rotatable head in proximity to said deposits;
   rotating said rotatable head relative to the balloon catheter while pushing the head into contact with the deposits to form an entryway for the dilatation catheter through the deposits; and
   inserting the balloon through the entryway opened by the rotatable drive and inflating the balloon to widen a flowpath for blood to flow through said vessel.

3. The process of claim 2 wherein as the drive rotates the head and the head is pushed through the deposits the elongated dilatation catheter is used to guide the rotating head and prevent unwanted side to side movement of said rotating head.

4. A catheter system for cannulizing a blood vessel to increase blood flow through said blood vessel comprising:
 (a) a flexible dilatation catheter having
  (i) a balloon at its distal end for expanding the blood vessel,
  (ii) an intermediate sheath defining a center passageway in communication with the blood vessel interior, and,
  (iii) a proximal fitting outside a patient body having a first input in communication with the center passageway and a second input in fluid communication with the balloon;
 (b) a drive catheter for insertion into the intermediate sheath of the flexible dilatation catheter and having a distal end defining a rotatable head for opening a lumen through deposits in the blood vessel, an elongated drive wire attached to the rotatable head for rotating the head, a sleeve for rotatably supporting the drive wire, a seal carried by the sleeve for impeding fluid entering a distal end of the sleeve from flowing out a proximal end of the sleeve and a coupling attached to a proximal end of said drive wire to rotate the drive wire;
 (c) an adapter to mate with the dilatation catheter fitting and route the drive catheter into the central passageway of the dilatation catheter, said adapter including a seal to prevent fluid in the central passageway from leaking out the adapter along an outer surface of the drive catheter;
 (d) drive means for rotating the drive catheter coupling to effect a rotation of the rotating head; and
 (e) means for inflating the balloon by directing a fluid into said balloon through said second input after the balloon is pushed into the lumen formed by the rotating head.

5. The catheter system of claim 4 wherein the adapter defines a side branch in fluid communication with the central passageway of the dilatation catheter with the adapter is connected to said fitting.

6. The catheter system of claim 4 wherein the seal comprises a plastic sleeve heat treated to conform to an outer surface of the drive wire and a proximal end of tee sleeve for allowing high speed rotation of the drive wire with minimal frictional interference between the seal and the drive wire.

7. A catheter system for cannulizing a blood vessel to increase blood flow through said blood vessel comprising:
 (a) a flexible dilatation catheter having a balloon at its distal end for expanding the blood vessel, an intermediate sheath defining a first passageway in communication with the blood vessel interior and a second passageway in communication with the balloon, and a fitting positioned outside a patient body when the dilatation catheter is in use, said fitting having a first input in communication with the center passageway of the intermediate sheath and a second input in fluid communication with the second passageway;
 (b) an elongated drive catheter for insertion into and through the first passageway of the flexible catheter and having a distal end defining a head for opening a lumen through blood vessel obstructions, an elongated intermediate drive wire for rotating the head as the head is brought into contact with the obstructions, an elongated bearing supporting the drive wire for rotation and a coupling attached to a proximal end of said drive wire to rotate the drive wire; said drive wire and coiled wire bearing having a length sufficient to position the distal head of said drive catheter beyond a distal end of the dilatation catheter as the coupling rotates the drive wire;
 (c) drive means for rotating the coupling and drive wire relative said bearing to effect a rotation of the head; and
 (d) means for inflating the balloon after the balloon is pushed into the lumen formed by the rotating head.

8. The catheter system of claim 7 additionally comprising an adapter to mate with the fitting and route the drive catheter into the first passageway, said adapter including a seal to prevent fluid in the first passageway of the dilatation catheter from leaking out the adapter along an outer surface of the drive catheter.

9. The catheter system of claim 7 wherein the bearing comprises a coiled wire bearing that rotatably supports a substantial length of said drive wire.

* * * * *